(12) United States Patent
Schwarz et al.

(10) Patent No.: US 10,576,281 B2
(45) Date of Patent: Mar. 3, 2020

(54) COCHLEAR IMPLANT FITTING VIA EFFERENT NERVE FIBERS

(71) Applicant: MED-EL Elektromedizinische Geraete GmbH, Innsbruck (AT)

(72) Inventors: Konrad Eugen Schwarz, Axams (AT); Angelika Dierker, Innsbruck (AT); Martin Franz Goll, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 179 days.

(21) Appl. No.: 15/791,728

(22) Filed: Oct. 24, 2017

(65) Prior Publication Data
US 2018/0043160 A1 Feb. 15, 2018

Related U.S. Application Data

(63) Continuation of application No. 14/989,964, filed on Jan. 7, 2016, now Pat. No. 9,795,785.
(Continued)

(51) Int. Cl.
*A61N 1/36* (2006.01)
*A61B 5/00* (2006.01)

(52) U.S. Cl.
CPC ..... *A61N 1/36036* (2017.08); *A61N 1/36039* (2017.08); *A61B 5/4052* (2013.01)

(58) Field of Classification Search
CPC .............. A61N 1/0541; A61N 1/36032; A61N 1/36036; A61N 1/36038; A61N 1/36039;
(Continued)

(56) References Cited

U.S. PATENT DOCUMENTS 7,818,052 B2  10/2010  Litvak et al.
9,795,785 B2  10/2017  Schwarz et al.
(Continued)

FOREIGN PATENT DOCUMENTS

| WO | 2005122887 A2 | 12/2005 |
| WO | 2013142846 A1 | 9/2013 |
| WO | 2015000528 A1 | 1/2015 |

OTHER PUBLICATIONS

Brown et al., "Electrically Evoked Whole Nerve Action Potentials in Ineraid Cochlear Implant Users: Responses to Different Stimulating Electrode Configurations and Comparison to Psychophysical Responses," Journal of Speech and Hearing Research, vol. 39, pp. 453-467, Jun. 1996.
(Continued)

*Primary Examiner* — Eugene T Wu
(74) *Attorney, Agent, or Firm* — Sunstein Kann Murphy & Timbers LLP

(57) ABSTRACT

A method of fitting a cochlear implant in an ipsilateral ear of a subject, the cochlear implant having an electrode array with one or more electrode contacts, includes applying broad-band white noise stimulus to a contralateral ear in order to mask efferent nerve fibers, applying a single pulse stimulus to the ipsilateral ear and then measuring base-line evoked compound action potential (CAP) signals in the ipsilateral ear for an electrode contact during a refractory period, applying a sequence of separated single pulse stimuli to the contralateral ear and then measuring attenuated CAP signals in the ipsilateral ear for the electrode contact during the refractory period, comparing the measured attenuated CAP signals to the measured base-line CAP signals in order to determine a CAP threshold for the electrode contact and adjusting processing parameters of the cochlear implant based on the CAP threshold.

17 Claims, 10 Drawing Sheets

Related U.S. Application Data

(60) Provisional application No. 62/101,429, filed on Jan. 9, 2015.

(58) Field of Classification Search
CPC ....... A61B 5/04001; A61B 5/12; A61B 5/121; A61B 5/125; A61B 5/4005; A61B 5/4041; A61B 5/4052; A61B 5/4887; A61B 5/4893
See application file for complete search history.

(56) References Cited

U.S. PATENT DOCUMENTS

| | | |
|---|---|---|
| 2005/0261748 A1 | 11/2005 | van Dijk |
| 2012/0245655 A1 | 9/2012 | Spitzer et al. |
| 2015/0341731 A1 | 11/2015 | Polak |
| 2015/0342505 A1 | 12/2015 | Lodwig et al. |
| 2016/0096020 A1 | 4/2016 | Smith |
| 2016/0151629 A1 | 6/2016 | Chalupper et al. |

OTHER PUBLICATIONS

Gantz, et al., "Intraoperative Measures of Electrically Evoked Auditory Nerve Compound Action Potential," The American Journal of Otology, vol. 15, No. 2, pp. 137-144, Mar. 1994.

Guinan, "Olivocochlear Efferents: Anatomy, Physiology, Function, and the Measurement of Efferent Effects in Humans," Ear & Hearing, vol. 27, No. 6, pp. 589-607, Dec. 2006.

Liberman, "Rapid assessment of sound-evoked olivocochlear feedback: Suppression of compound action potentials by contralateral sound," Hearing Research, vol. 38, pp. 47-56, 1989.

Puria, et al., "Olivocochlear reflex assays: Effects of contralateral sound on compound action potentials versus ear canal distortion products," J. Acoust. Soc. Am., vol. 99, No. 1, pp. 500-507, Jan. 1996.

Wittekindt, "Investigating the efferent influence on the inner ear by measuring otoacoustic emissions," Doctoral Thesis, Dissertation, 125 pages, Aug. 26, 2009 (in German) (English abstract attached, 2 pages).

International Searching Authority, International Search Report—International Application No. PCT/US2016/012413, dated Apr. 14, 2016, together with the Written opinion, 12 pages.

Relative latencies

Stimulation electrode at test side

|   | E1 | E2 | E3 | E4 | E5 | E6 | ... |
|---|---|---|---|---|---|---|---|
| E1 | 1.7 | 1.6 | 1.4 | 1.3 | 1.0 | 0.9 | |
| E2 | 1.4 | 1.6 | 1.5 | 1.2 | 1.0 | 1.0 | |
| E3 | 1.1 | 1.5 | 1.7 | 1.3 | 1.0 | 1.0 | |
| E4 | 1.0 | 1.2 | 1.6 | 1.8 | 1.5 | 1.1 | |
| E5 | 1.0 | 1.1 | 1.4 | 1.7 | 1.7 | 1.5 | |
| E6 | 1.0 | 1.0 | 1.2 | 1.4 | 1.5 | 1.8 | |

Stimulation electrode at masker side

*FIG. 10A*

Relative amplitudes

Stimulation electrode at test side

|   | E1 | E2 | E3 | E4 | E5 | E6 | ... |
|---|---|---|---|---|---|---|---|
| E1 | 0.3 | 0.6 | 0.8 | 1.0 | 1.0 | 1.0 | |
| E2 | 0.6 | 0.4 | 0.6 | 0.9 | 1.0 | 1.0 | |
| E3 | 1.0 | 0.6 | 0.4 | 0.7 | 0.8 | 1.0 | |
| E4 | 1.0 | 1.0 | 0.6 | 0.4 | 0.7 | 0.9 | |
| E5 | 1.0 | 1.0 | 0.8 | 0.5 | 0.3 | 0.6 | |
| E6 | 1.0 | 1.0 | 0.9 | 0.7 | 0.5 | 0.3 | |

Stimulation electrode at masker side

COCHLEAR IMPLANT FITTING VIA EFFERENT NERVE FIBERS

CROSS REFERENCE TO RELATED APPLICATIONS

The present application is a continuation of U.S. patent application Ser. No. 14/989,964 filed Jan. 7, 2016, now U.S. Pat. No. 9,795,785, which claims the benefit of U.S. Provisional Patent Application No. 62/101,429 filed Jan. 9, 2015, the disclosures of which are incorporated by reference herein in its entirety.

TECHNICAL FIELD

The present invention relates to implant fitting by sensing neural tissue responding to electrical stimulation signals, especially for hearing implant systems such as cochlear implant systems.

BACKGROUND ART

FIG. 1 schematically shows the anatomy of a normal human ear. The ear typically transmits sounds, such as speech sounds, through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. The cochlea 104 includes three chambers along its length, an upper chamber known as the scala vestibuli, a middle chamber known as the scala media, and a lower chamber known as the scala tympani. The cochlea 104 forms an upright spiraling cone with a center called the modiolus where the axons of the auditory nerve 113 reside. In response to received sounds transmitted by the middle ear 103, the fluid-filled cochlea 104 functions as a transducer to convert mechanical motion and energy and, in response, to generate electric pulses which are transmitted to the auditory nerve 113, and ultimately to the brain.

Hearing is impaired when there are problems in the transducer function within the inner ear to transduce external sounds into meaningful action potentials along the neural substrate of the cochlea 104. To improve impaired hearing, there are several types of auditory prostheses that have been developed, such as cochlear implants, brainstem-implants, midbrain-implants or cortical implants, that electrically stimulate auditory nerve tissue with small currents delivered by multiple electrode contacts distributed along an implant electrode. The cochlear implant typically includes an electrode carrier having an electrode lead 109 and an electrode array 110, which is threaded into the cochlea 104. For brain-stem, midbrain and cortical implants, the electrode array is located in the auditory brainstem, midbrain or cortex, respectively. These electrodes may also be used for sensing neural tissue response signals, i.e., function as measurement electrodes.

FIG. 1 shows some components of a typical cochlear implant system where an external microphone provides an audio signal input to an external signal processor 111 which implements one of various known signal processing schemes. The processed signal is converted by the external signal processor 111 into a digital data format, such as a sequence of data frames, for transmission by an external coil 107 into a receiving stimulator processor 108. Besides extracting the audio information, the receiving stimulator processor 108 may perform additional signal processing, such as error correction, pulse formation, etc., and produces a stimulation pattern (based on the extracted audio information) that is sent through the electrode lead 109 to the implanted electrode array 110. Typically, the electrode array 110 includes multiple stimulation contacts 112 on its surface that provide selective electrical stimulation of the cochlea 104.

For an audio prosthesis, such as a cochlear implant, to work correctly, some patient-specific operating parameters need to be determined in a fit adjustment procedure where the type and number of operating parameters are device dependent and stimulation strategy dependent. In some cases, the fitting is based on subjective responses from the patient, where the behavioural thresholds (T-level) and maximum comfort levels (C-levels) are determined. If the user is uncooperative or has extremely limited expressive language skills (e.g., very young children), the subjective responses are not sufficient for fitting. Objective physiological measures can assist in such cases. For example, the electrically evoked stapedial reflex (ESR), the electrically evoked auditory brainstem response (EABR), and the electrically evoked compound action potential (eCAP) are objective measures that may be used to assess the auditory nerve response to electrical stimulation.

To collect information about the electrode—nerve interface, a commonly used objective measurement is based on the measurement of Neural Action Potentials (NAPs) such as the electrically-evoked Compound Action Potential (eCAP), as described by Gantz et al., *Intraoperative Measures of Electrically Evoked Auditory Nerve Compound Action Potentials*, American Journal of Otology 15 (2):137-144 (1994), which is incorporated herein by reference in its entirety. The eCAP is a measure of electrically elicited synchronous VIII nerve (auditory nerve) activity, and eCAP measures are performed by stimulation with a single pulse, where the signal is recorded over time after stimulus. In this approach, the recording electrode is usually placed at the scala tympani of the inner ear. The overall response of the auditory nerve to an electrical stimulus is measured typically very close to the position of the nerve excitation. This neural response is caused by the super-position of single neural responses at the outside of the auditory nerve membranes.

These recordings show characteristic minima (N1, N2) and maxima (P1, P2, P3), where the difference in amplitude between P2–N1 (eCAP-amplitude) of the recorded signal is of special interest. FIG. 2 shows an example of measuring eCAP amplitude based solely on time since stimulation for a single response signal recording. The response signal is characterized by the amplitude between the minimum voltage (this peak is called typically N1) and the maximum voltage (peak is called typically P2), the so-called local extrema. These extrema among others represent the most prominent physiological landmarks of the ECAP signal. The amplitude of the eCAP at the measurement position is in most cases between approximately 10 µV and 1800 µV. One eCAP recording paradigm is the "amplitude growth function," as described by Brown et al., *Electrically Evoked Whole Nerve Action Potentials In Ineraid Cochlear Implant Users: Responses To Different Stimulating Electrode Configurations And Comparison To Psychophysical Responses*, Journal of Speech and Hearing Research, vol. 39:453-467 (June 1996), which is incorporated herein by reference in its entirety. This function is the relation between the amplitude of the stimulation pulse and the peak-to-peak voltage of the eCAP.

The eCAP threshold is determined based on amplitude-growth functions or via expert systems using the correlation of the measured eCAP signal towards templates of typical noise and clear responses (see, e.g., U.S. Pat. No. 7,818,052 and International Appl. No. PCT/US2005/021207). Amplitude growth functions (AGF) are a sequence of measurements with increasing stimulation intensity, and since the eCAP-amplitude increases, the input (stimulation intensity)/output (eCAP amplitude) function (usually estimated by a linear function: out=in*eCAP slope+eCAP offset) can be used to extrapolate the maximal stimulation intensity where no eCAP signal is present, the eCAP threshold. Expert systems increase the stimulation intensity successively until a signal is present, and the minimal stimulation intensity necessary yields the eCAP threshold. eCAP based measures are affected by efferent and afferent nerve fibers, where only afferent fibers contribute to the auditory percept. To elicit an eCAP which can be recorded, the necessary minimal strength of the corresponding stimulus might be up to about 11 charge units (~nano coulomb) at a rate ~40 Hz (see, e.g., MAESTRO Software 4.1, ART-task, at 10 ms Measurement Gap). In a post-operative scenario, this might result for some individuals in a too loud perception.

One common method for fit adjustment in a cochlear implant is to behaviorally find the auditory threshold (THR) and maximum comfortable loudness (MCL) value for each separate electrode contact. For this, the stimulation charge on a selected electrode channel is usually increased in steps from zero until the THR or MCL level is reached in a subjective procedure (e.g., method of adjustments) or an objective procedure (e.g., eCAP or ESR). This increase can be either stimulation burst duration or stimulation burst amplitude or a combination thereof. For this procedure, constant amplitude stimulation bursts with about 10-1000 msec duration are usually utilized. See, e.g., Rätz, *Fitting Guide for First Fitting with MAESTRO* 2.0, MED-EL, Fürstenweg 77a, 6020 Innsbruck, 1.0 Edition, 2007. AW 5420 Rev. 1.0 (English_EU); incorporated herein by reference in its entirety. Typically, each electrode channel is fitted separately without using the information from already fitted electrode channels.

Behavioural thresholds and maximum comfort levels are determined using pulse trains. If the frequency or the current (for single pulses within the pulse train) is increased, the stimulation of the auditory nerve by the pulse train is louder for the cochlear implant user. The individual loudness (reported by the cochlear implant user) plotted against increasing frequency or current is called the behavioural loudness growth function (LGF). The linkage between subjective loudness perception and eCAP threshold is done using adjustment factors: linear dependency of THR with MCL using fixed values, eCAP threshold and eCAP slope.

Some patient-specific operating parameters for a cochlear implant include:

$THR_1$ (lower detection threshold of stimulation amplitude) for Electrode Contact 1
$MCL_1$ (most comfortable loudness) for Electrode Contact 1
Phase Duration for Electrode Contact 1
Amplitude for Electrode Contact 1
Pulse Rate for Electrode Contact 1
$THR_2$ for Electrode Contact 2
$MCL_2$ for Electrode Contact 2
Phase Duration for Electrode Contact 2
Amplitude for Electrode Contact 2
Pulse Rate for Electrode Contact 2
Compression Parameters of frequency, e.g., electrode contact mapping
Parameters describing the electrical field distribution, e.g., spatial spread Another common method for fit adjustment in a cochlear implant is to "frequency match" the implant in one ear with the other, contralateral ear in order to enable the auditory system to detect correctly Interaural Level Differences (ILD) and Interaural Time Differences (ITD) since the signal process of both ears is connected. Localization of sound is influenced by ILD and ITD cues, but in general pitch cues are regarded as the most important factors affecting the performance of cochlear implant users. Currently, the bilateral matching of pitch is done by matching pitch to electrodes solely based on subjective measures.

SUMMARY OF THE EMBODIMENTS

In accordance with one embodiment of the invention, a method of fitting a cochlear implant in a subject in order to frequency match the cochlear implant includes applying a tonal stimulus to a contralateral ear in order to mask efferent nerve fibers, measuring evoked compound action potential (CAP) signals in an ipsilateral ear during a refractory period, and measuring CAP signals in the ipsilateral ear outside of the refractory period. The method further includes comparing the measured CAP signals during the refractory period to the measured CAP signals outside of the refractory period in order to determine a stimulation location on the cochlear implant that corresponds to a location in the ipsilateral ear that responds to a frequency of the tonal stimulus applied to the contralateral ear, and adjusting processing parameters of the cochlear implant based on the stimulation location.

In accordance with another embodiment of the invention, a system for fitting a cochlear implant in a subject in order to frequency match the cochlear implant includes a tissue stimulation device configured to generate a tonal stimulus to mask efferent nerve fibers in the subject and one or more response measurement contacts configured to measure evoked compound action potential (CAP) signals during a refractory period and outside of the refractory period. The system further includes a frequency matching module in communication with the one or more response measurement contacts and configured to receive the CAP signals during the refractory period and outside of the refractory period and to determine a stimulation location on the cochlear implant based on a comparison of the received CAP signals during the refractory period and the received CAP signals outside of the refractory period and a parameter adjusting module in communication with the frequency matching module and configured to interface with the cochlear implant and to adjust processing parameters of the cochlear implant based on the stimulation location.

In some embodiments, the tonal stimulus may be applied by an acoustical, mechanical or electrical stimulation. The electrical stimulation may be applied with a second cochlear implant in the contralateral ear. The method may further include applying stimulation to the ipsilateral ear before measuring the CAP signals during the refractory period or outside of the refractory period. The method may further include applying a second tonal stimulus to the contralateral ear before measuring the CAP signals during the refractory period. The stimulation location on the cochlear implant may be between two stimulation contacts. The method may further include applying the tonal stimulus to the ipsilateral ear in order to mask efferent nerve fibers, measuring the CAP signals in the contralateral ear during a refractory period and outside of a refractory period, and comparing the measured CAP signals in the contralateral ear during the refractory period to the measured CAP signals in the contralateral ear outside of the refractory period in order to verify the processing parameters are correctly adjusted. The tissue stimulation device may be an acoustical device configured to deliver an acoustical stimulus to an outer or middle ear. The tissue stimulation device may be a mechanical device configured to deliver a mechanical stimulus to an outer ear or skull. The mechanical device may include a bone conduction transducer. The tissue stimulation device may be a stimulation electrode configured to deliver an electrical stimulus to neural tissue of an inner ear. The system may further include a second cochlear implant that includes the stimulation electrode configured to deliver the electrical stimulus to the neural tissue of the inner ear. The tissue stimulation device may be configured to generate two or more tonal stimuli to mask the efferent nerve fibers in the subject. The cochlear implant may include the one or more response measurement contacts configured to measure the CAP signals. The system may further include a tissue stimulation module in communication with the tissue stimulation device and configured to generate one or more tonal stimulation signals that are sent to the tissue stimulation device. When the tissue stimulation device is a second cochlear implant, the second cochlear implant may include one or more response measurement contacts in communication with the frequency matching module and configured to measure CAP signals, the cochlear implant may be configured to generate a tonal stimulus to mask efferent nerve fibers in the subject, and the frequency matching module may be configured to receive the CAP signals from the cochlear implant and the second cochlear implant in order to verify that the processing parameters are appropriately adjusted in the cochlear implant.

BRIEF DESCRIPTION OF THE DRAWINGS

FIGS. 10A and 10B show exemplary relative values for amplitudes and latencies for measurements with masking stimuli on different electrodes at the masking side according to embodiments of the present invention.

DETAILED DESCRIPTION

Figure 1:
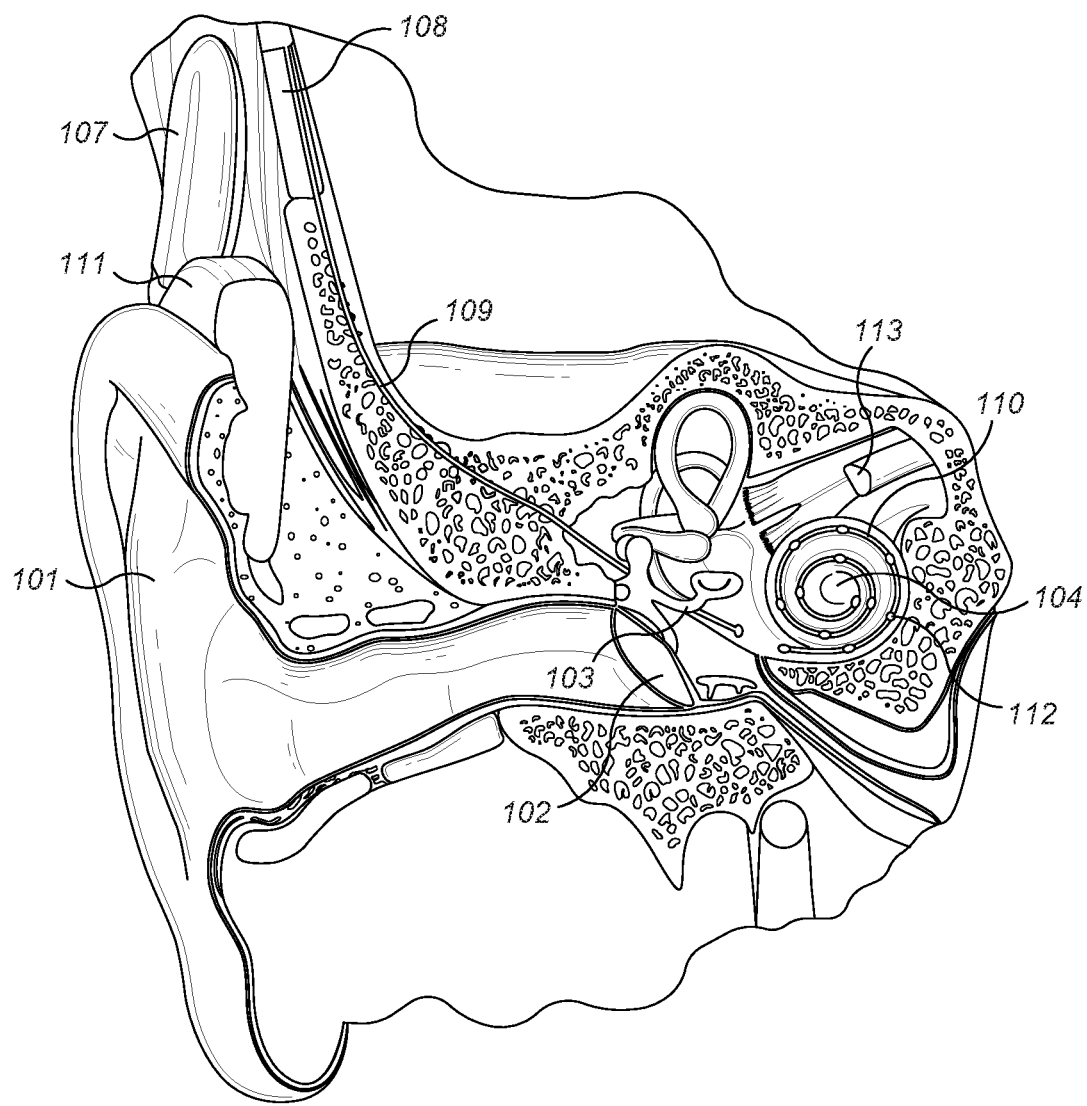
FIG. 1 shows anatomical structures of a human ear having a cochlear implant system.
Figure 2:
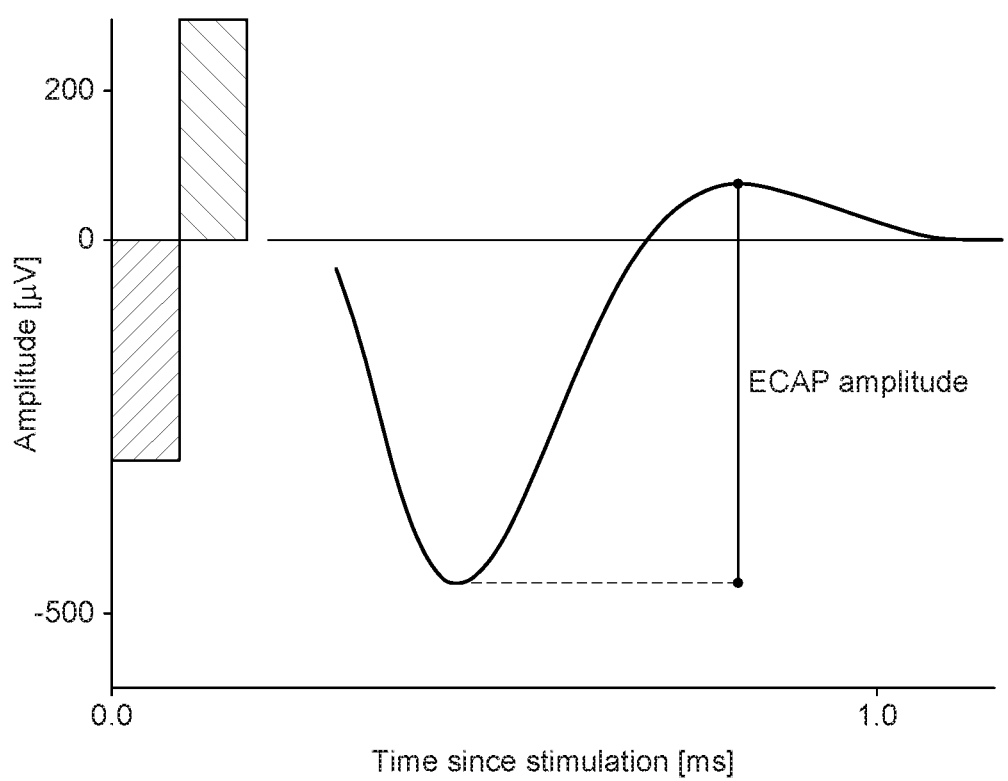
FIG. 2 shows an example of measuring eCAP amplitude based solely on time since stimulation for a single response signal recording.
Figure 3:
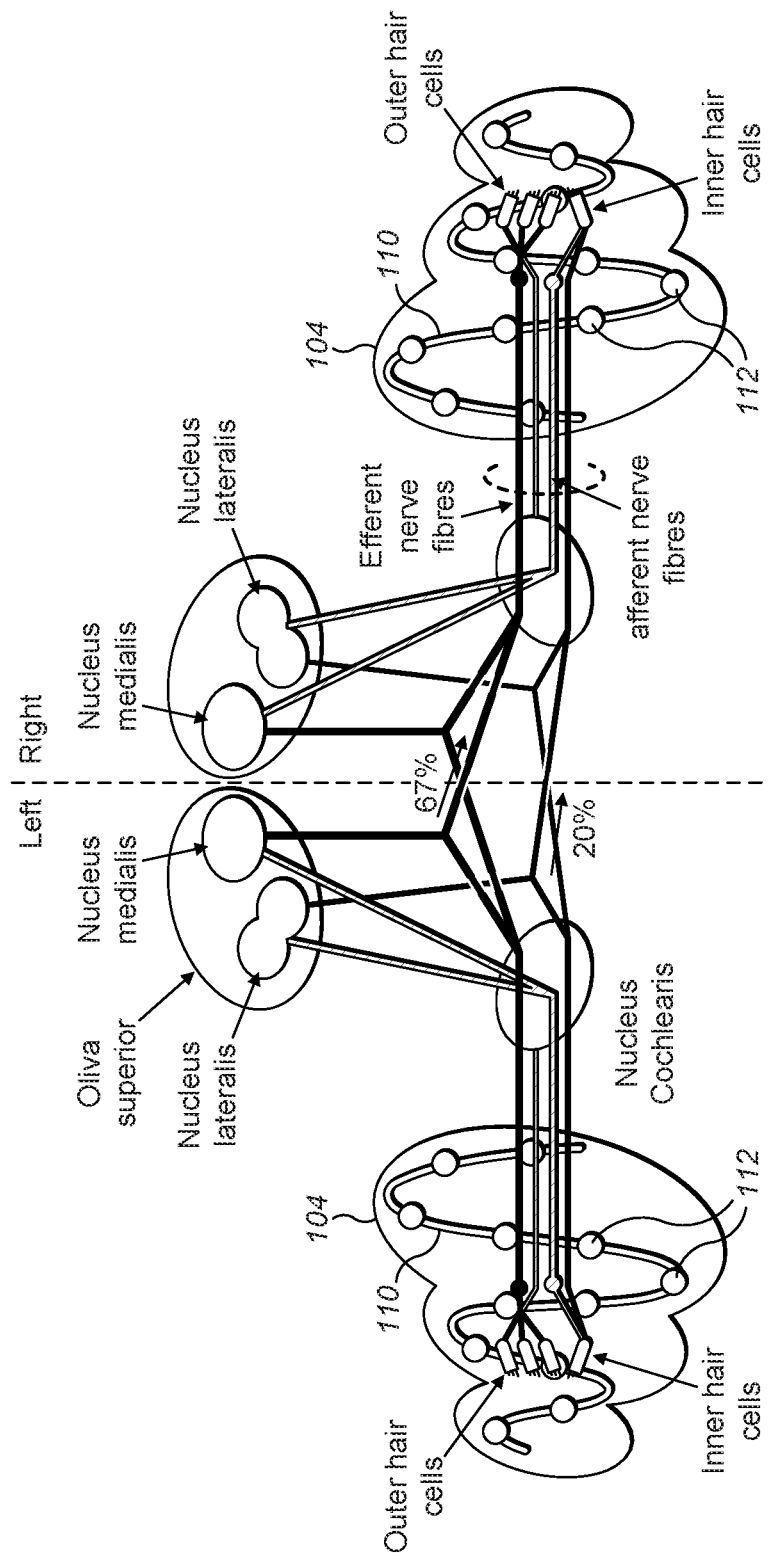
FIG. 3 shows a schematic view of the auditory anatomy showing the afferent and efferent nerve fibers along with the Nucleus Cochlearis, the Oliva Superior (especially Nucleus medialis and Nucleus lateralis) and the cochlear.

Embodiments of the present invention are directed to systems and methods of fitting a cochlear implant in a subject in order to frequency-match the cochlear implant with the other ear. Embodiments make use of the intra-aural pathways of the auditory system (such as shown in FIG. 3) in order to measure patient-specific operating parameters objectively, such as frequency matching, in a cochlear implant. A considerable part of efferent fibers within the auditory nerve can be masked by contralateral stimulation (acoustical or electrical) due to the connection of both cochleae via afferent and efferent neurons to the olivocochlear bundle. Embodiments of the present invention compare neural answers to ipsilateral cochlear responses with contralateral stimuli to neural answers to ipsilateral responses without contralateral stimuli. The difference between both responses is considered to be due to the connection of the intraaural pathways. Therefore, applying a stimulus at a certain frequency, e.g., F1, at a contralateral site masks efferent fibers of that frequency at the ipsilateral, tested site and thus reduces the eCAP signal and changes the measured voltage at the corresponding frequency, e.g., F1, at the tested site that includes the cochlear implant. Embodiments then determine the location on the cochlear implant that corresponds to the location of maximum reduced response in the ipsilateral ear and correlates that implant location to the ear location in order to frequency-match the ipsilateral, tested ear with the cochlear implant to the other, contralateral ear. The frequency matching may then be verified by switching the tested site and the contralateral site and repeating the stimulation and measuring process. Details of illustrative embodiments are discussed below.

FIG. 3 shows the auditory anatomy with the afferent and efferent nerve fibers (shown with hashed lines slanted in two different directions) along with the Nucleus Cochlearis, the Oliva Superior (including Nucleus medialis and Nucleus lateralis) and the cochlear 104. The efferent nerve fibers are depicted with the signal from the Oliva superior to the hair cells. The strength of signals sent from the oliva superior to the contralateral ear is quantified to be roughly about ⅔ of all efferent fibers associated with outer hair cells originating in the medial olivocochlear (MOC) and 20% of those originating in the lateral olivocochlear (LOC) neurons. It is believed that roughly ⅓ of all efferent fibers associated with outer hair cells are elicited most effectively by contralateral stimuli, and ⅔ by ipsilateral stimuli. The number of neurons associated with the outer hair cells is believed to be about 10% of the total number of neurons for healthy cochleae. For degenerated cochleae, the relative number of the nerve fibers associated with outer hair cells increases since mainly the neurons associated with inner hair cells degenerate. In the case of severe sensorineural deafness, it is believed that the fibers associated with outer hair cells persist in greater numbers than the ones associated with inner hair cells, since these nerve fibers seem to be more resistant to retrograde degeneration. Based on these studies, the attenuation of the CAP amplitude is expected to be in the range 3-20% (about 30% for severe neural deafness) for humans affected by hearing loss. The strength of attenuation varies for each individual, and subjects with low CAP suppression show a lower discharge rate (depending on refractory times) of efferent nerve fibers. If tones are used for the stimulus on the contralateral side, rather than noise, CAP suppression varies with frequency. The most effective frequency is dependent on the frequency of ipsilateral stimuli. In general, the higher the frequency of ipsilateral stimuli, the less effective the contralateral masking with frequency matched tones is expected.

Figure 4:
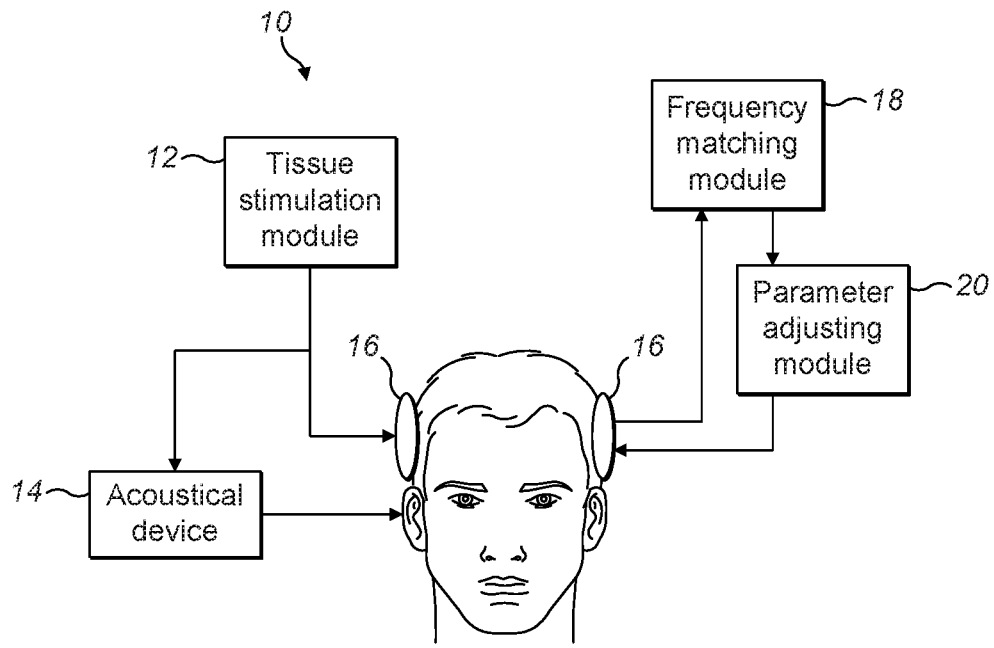
FIG. 4 shows a frequency matching system for fitting a cochlear implant in a subject according to embodiments of the present invention.
Figure 4A:
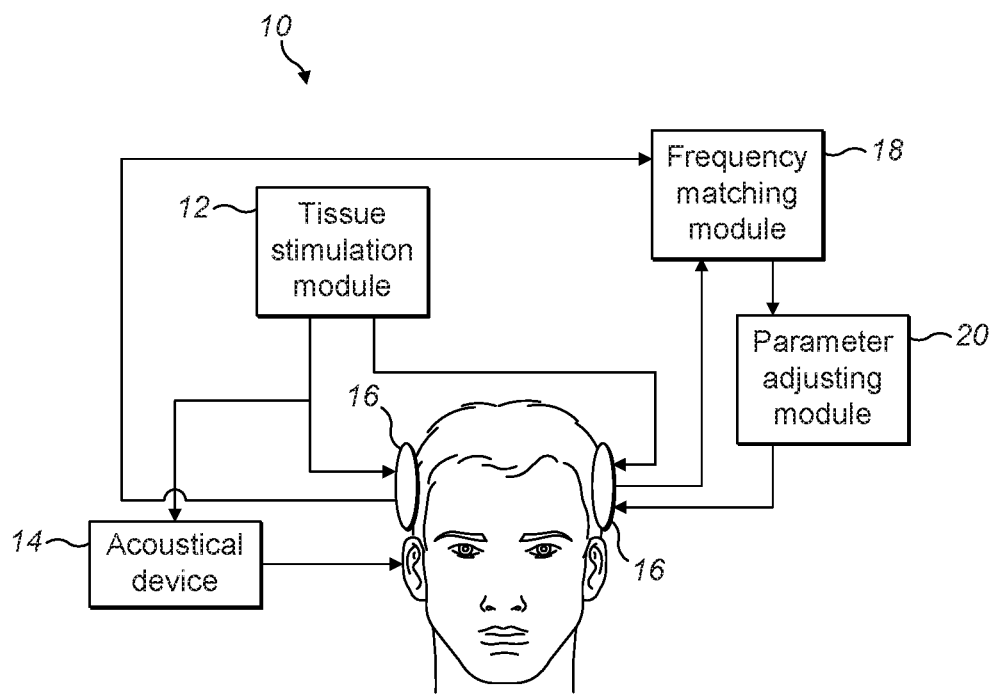
FIG. 4A shows another configuration for a frequency matching system for fitting a cochlear implant according to embodiments of the present invention.
Figure 5:
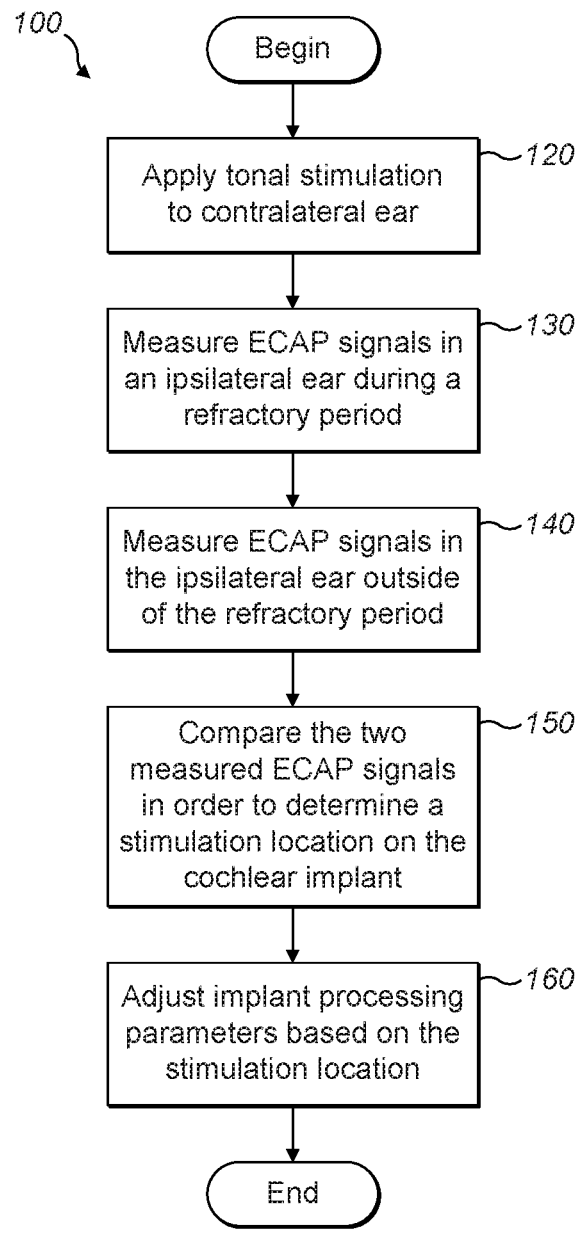
FIG. 5 shows a method of frequency matching a cochlear implant according to embodiments of the present invention.

FIG. 4 shows a frequency matching system 10 for fitting a cochlear implant and FIG. 5 shows a method of frequency matching 100 a cochlear implant according to embodiments of the present invention. FIG. 4A shows a frequency matching system 10 configuration that includes a verification process. As described below, embodiments of the system and method are used with a contralateral ear or "masker side" that is sensitive to acoustical stimuli or supported with a cochlear implant and with an ipsilateral ear or "test side" that is supported with a cochlear implant to be fitted. In addition, the system applies a tonal stimulus, which is a frequency specific pure tone or single frequency, or a set of pure tones or frequencies.

The frequency matching system 10 includes a tissue stimulation module 12 that generates one or more tonal stimulation signals that are sent to a tissue stimulation device, such as an acoustical device 14 or a cochlear implant 16. The tissue stimulation device 14, 16 then generates an acoustical stimulus or an electrical stimulus of one or more tones or frequencies and applies the tonal stimulus to a contralateral ear or masker side (step 120) in order to mask efferent nerve fibers. As known by those skilled in the art, masked nerve fibers are those fibers that have been stimulated, in this case at a certain frequency, and are unable to provide an additional evoked response until a refractory period has ended. Thus, masked nerve fibers provide no additional neural response during their refractory period. Consequently, any CAP measure during this refractory period for the ear to be frequency matched will not measure the signal contribution from the masked efferent nerve fibers, and the CAP measured is therefore reduced by this amount.

Figure 6:
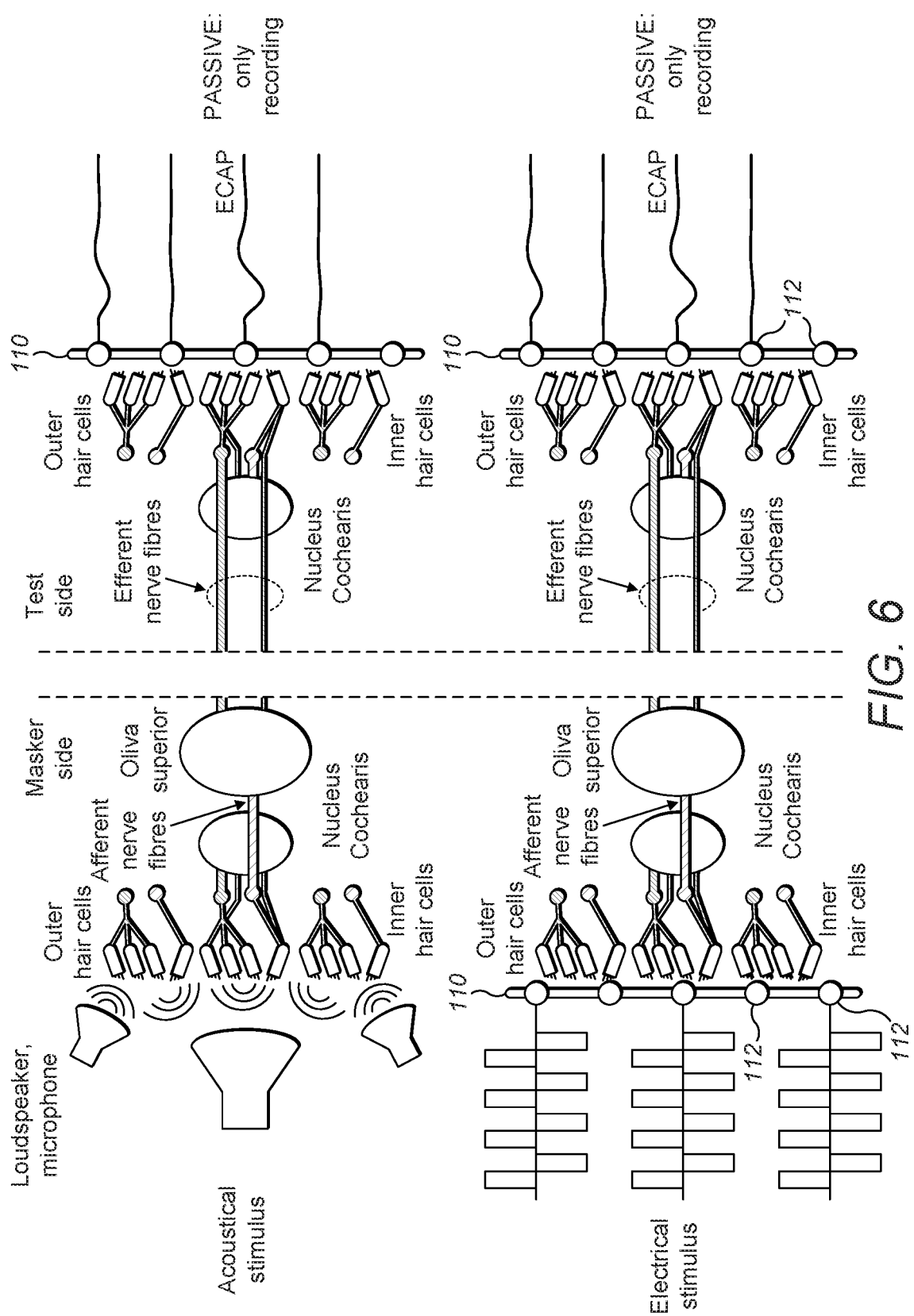
FIG. 6 shows a schematic view of a portion of a frequency matching system with an acoustical or electrical stimulus on a masker side and using a passive CAP testing procedure on a test side according to embodiments of the present invention.
Figure 7:
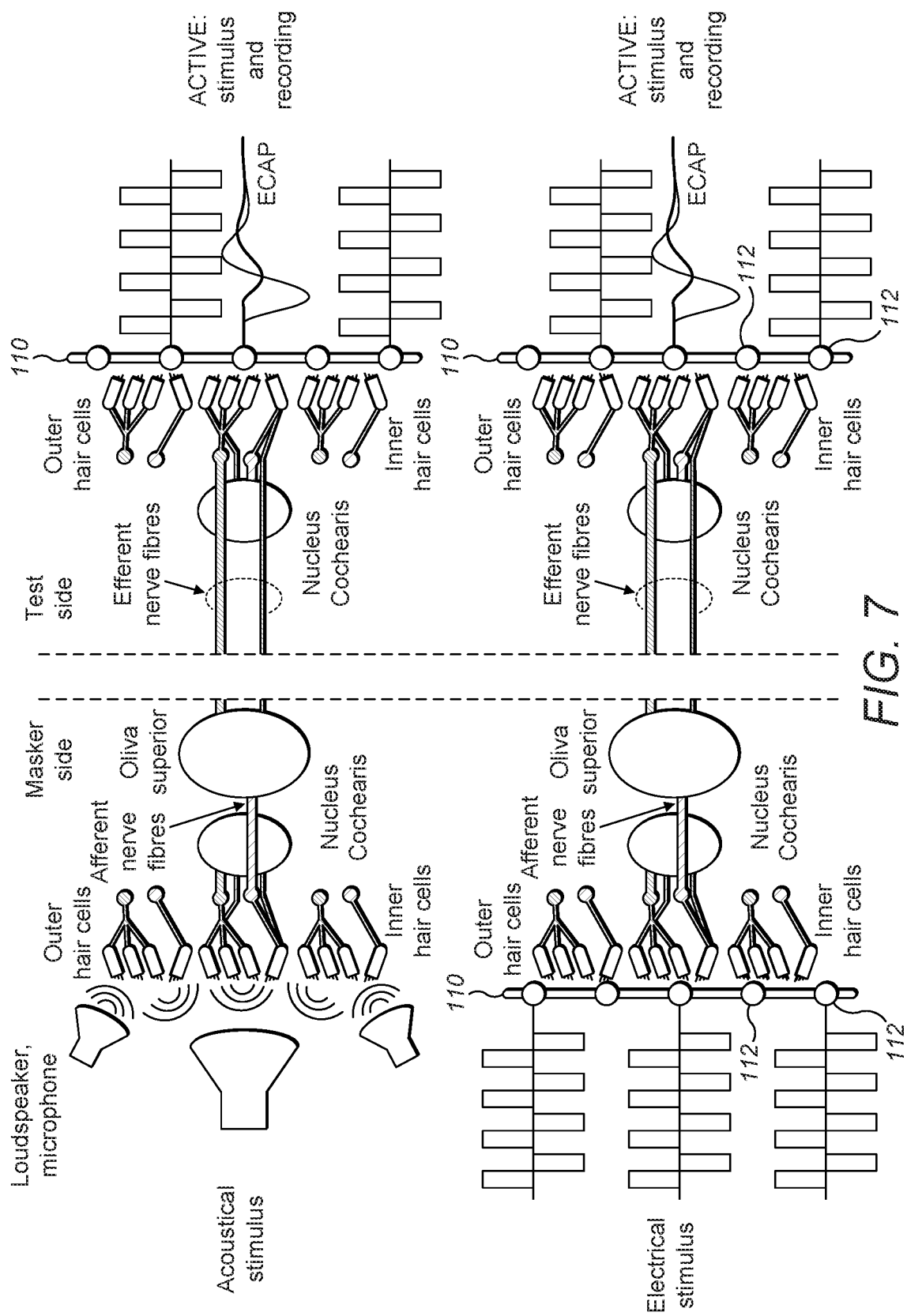
FIG. 7 shows a schematic view of a portion of a frequency matching system with an acoustical or electrical stimulus on a masker side and using an active CAP testing procedure on a test side according to embodiments of the present invention.

After the tonal stimulus is applied to the contralateral ear, the CAP signals are measured in an ipsilateral ear during a refractory period (step 130) and the CAP signals are measured in the ipsilateral ear outside of the refractory period (step 140). One or more response measurement contacts, such as stimulation contacts 112 on a stimulation electrode array 110 in the cochlear implant 16 to be fitted, are configured to measure the CAP signals during and outside of the refractory period. As shown in FIGS. 6 and 7, various testing configurations may be used to measure the CAP signals. For example, two main types of test scenarios may be used: passive testing, where only CAPs are recorded without ipsilateral stimulation, such as shown in FIG. 6, and active testing, where an ipsilateral stimulus is applied and a CAP is recorded, as shown in FIG. 7. Test stimuli may include stimulation with a single pulse or a sequence of pulses at a single electrode and recording at a second, or stimulation with multiple electrodes or stimuli and recording on multiple electrodes. The CAP signal recorded at the test side due to an ipsilateral stimulus only (without contralateral stimulation) is referred to as a "base-line" signal and an CAP recording where a contralateral stimulation takes place is referred to as an "attenuated" signal.

For masker stimuli, tones at certain frequencies are used. The stimuli may be applied acoustically, mechanically or electrically on multiple electrodes, as shown in FIGS. 6 and 7. If the cochlea where the masker stimuli are applied is hearing, i.e., sensitive to acoustical or mechanical stimuli, tone bursts at one or more selected frequencies may be applied using a standard loudspeaker with headphones or a microphone. Distortion Product Otoacoustic Emissions (DP-OAE) can be used to measure ipsilateral efferent signals and to verify ipsilateral activation of outer hair cells due to intact processing of the acoustical stimulus via the middle ear and the cochlea. The results help to quantify contralateral activation of outer hair cells. Since efferent processes affect the ipsilateral side as well, the magnitude of efferent processes can be measured for ipsilateral processes and can be estimated using DP-OAE for contralateral processes. If the cochlea where the masker stimuli are applied is supplied with a cochlear implant, tone bursts at one or more selected frequencies may be applied using that cochlear implant, and ipsilateral efferent signals may be estimated on behalf of CAP recordings following sequences of pulses, e.g., with rates >100 pulses/second.

In addition, various kinds of contralateral maskers may be used, as known by those skilled in the art, such as maskers of short duration (e.g., about 400 ms) and long durations (e.g., about 2-10 s). If short duration maskers are used (e.g., <1 s), the masker-signal on the contralateral ear is stopped before each test stimulus and CAP recording on the ipsilateral ear. After a period of time, the masker signal on the contralateral ear is restarted once the peripheral influence disappears (estimated to be about <0.5 s), and is stopped again for the next test stimuli on the ipsilateral ear. If long duration maskers are used (e.g., 2-13 s), the test stimuli and recordings can be performed during the 2-13 seconds and after the masker onset on the contralateral side. However, sequences of pulses exceeding a certain duration (e.g., few milliseconds) and/or a rate (e.g., >15 pulses/s) may possibly activate ipsilateral induced efferent processes. The strength of masker stimuli can be varied for both setups. For the long duration maskers, a strong masker (e.g., high amplitude, such as at MCL level) may be preferred. The ipsilateral applied test-stimuli may be preferably at moderate strength (e.g., about 50% of MCL) to show highest impact of attenuation.

Figure 8A:
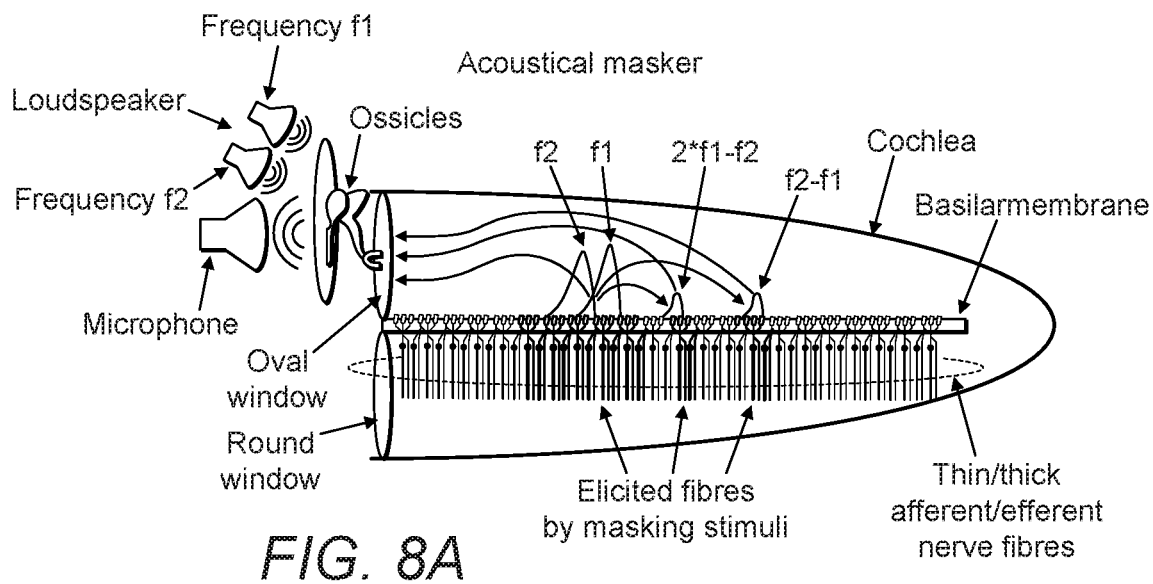
FIGS. 8A-8C show schematic views of a portion of a cochlea during a frequency matching process according to embodiments of the present invention.
Figure 8B:
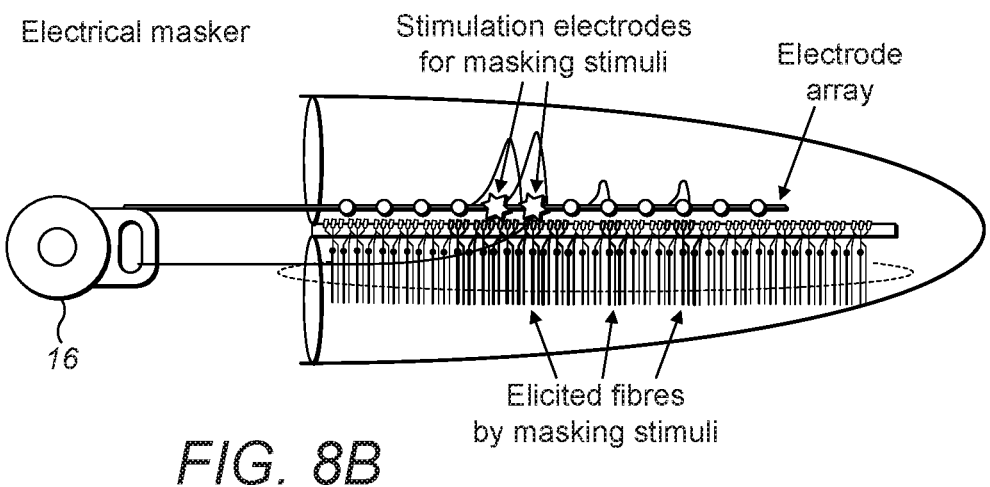
Figure 8C:
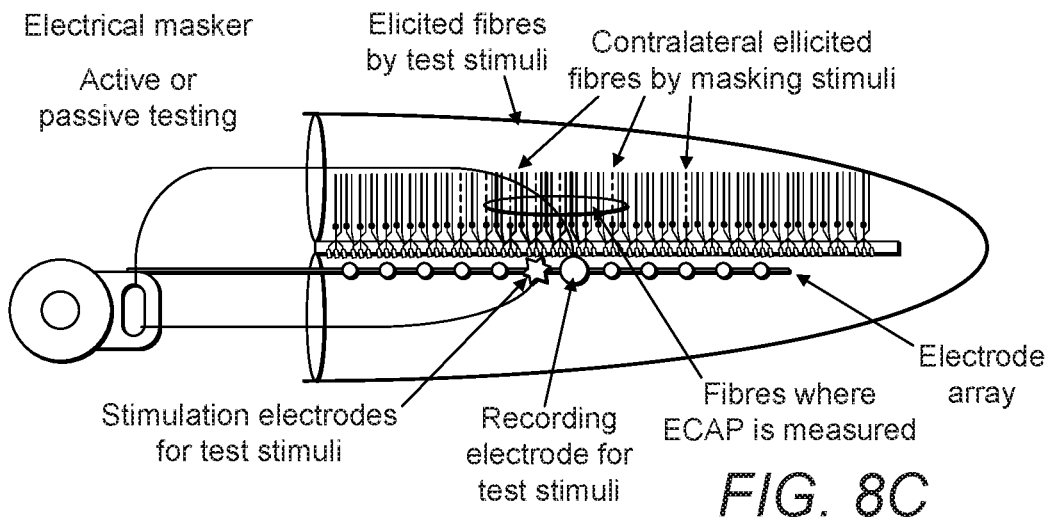

FIGS. 8A-8C show schematic views of a portion of a cochlea during a frequency matching process for different testing scenarios. FIG. 8A shows a test setup for an acoustical stimulation device 14, and the activation of outer hair cells with two different frequencies (frequencies f1 and f2, cubic distortion product 2*f1−f2). FIG. 8A shows a simplified view of the DP-OAE measurement of applying an acoustical masker. Besides the hair cells of the corresponding frequency regions for the applied stimuli (f1 and f2, f2>f1), outer hair cells corresponding to frequencies 2*f1−f2 (and f2−f1) are also elicited. FIG. 8B shows a simplified view of an electrical masker. Electrical stimulation takes place at two electrodes (referring to f1 and f2 of the example in FIG. 8A). For both masking conditions, nerve fibers (connected to inner and outer hair cells) are elicited. In FIG. 8C, the test conditions are sketched. For passive testing, no stimulation is applied on this ear. The eCAP corresponding to the elicited efferent nerve fibers is measured (for one, more or each electrode contact). For active testing, a stimulus is applied (shown here for a single electrode contact, but applied sequentially on all electrode contacts) and the eCAP is measured on a second electrode contact. For this setup, a "base-line" measurement without contralateral masking is compared to the "attenuated" measurement with contralateral stimulation. The largest effect on the eCAP signal is expected at the electrode contact which is closest to the masked fibers.

Referring again to FIGS. 4 and 5, a frequency matching module 18 compares the measured eCAP signals during the refractory period to the measured eCAP signals outside of the refractory period in order to determine a stimulation location on the cochlear implant (step 150) that corresponds to a location in the ipsilateral ear that responds to a frequency of the tonal stimulus applied to the contralateral ear. Since contralateral efferent pathways are tonotopically organized, the masking effect of the contralateral stimulus at a certain frequency (for comparison with DP-OAE: f2) is maximal at the frequency-matched region of the ipsilateral cochlea. Therefore, if single pulses at a single electrode are used to determine "base-line" and "attenuated" eCAPs (with sequences of single pulses) and to determine "base-line" and "attenuated" Amplitude Growth Functions (AGFs) and Recovery Functions (RFs), the magnitude of the masking effect can be determined by the difference in eCAP amplitude/latency of the "base-line" and "attenuated" eCAP, or the difference of the "base-line" and "attenuated" eCAP threshold with slope or the difference of the "base-line" and "attenuated" eCAP recovery. Therefore, the stimulation location on the cochlear implant that measures the biggest change or impact due to the contralateral masker is defined as "frequency-matched" to the applied masking signal.

A parameter adjusting module 20 adjusts processing parameters of the cochlear implant 16 to be fitted on the test side based on the stimulation location (step 160). After matching a stimulation electrode contact at the test side to a certain frequency or frequencies, the roles of masker and test side may be interchanged, and the frequency matching may be verified, such a configuration of the system 10 is shown in FIG. 4A. For example, in the case of a cochlear implant supported masker side, no difference in setup is needed except the roles of the two cochlear implants are interchanged. In the case of a hearing, i.e., sensitive to acoustical or mechanical stimuli, masker side, DP-OAE may be used. The process in steps 120 through 160 may be repeated for any number of frequencies until the cochlear implant 16 to be fitted is frequency mapped to the desired frequencies in the ipsilateral ear.

An illustrative example of one specific embodiment of a frequency matching process is described below. Cochlea "A" is supplied with a cochlear implant to be fitted. For each frequency of interest (if other cochlea "B" is stimulated with acoustical stimuli) or each electrode contact (if the other cochlea "B" is supported with a cochlear implant), the process may follow the steps below:

In order to determine the "base-line" signal, a predefined measurement setup is performed on all electrode contacts of cochlear implant in cochlea "A" in step 1, e.g., Amplitude Growth Functions and Recovery Functions using for example and without limitation:

a. Stimulation charge at ~20-25 qu may be varied over electrode contacts;
 b. 25-40 iterations; and
 c. Recording Electrode adjacent to Stimulation Electrode may be varied.

In order to determine the "attenuated" signals, a noise restricted to the chosen frequency or frequencies is applied on cochlea "B" with acoustical stimuli or electrical stimuli on the selected electrode contact(s) in step 2. The measurement setup, as in step 1, is applied on all electrode contacts of the cochlear implant in cochlea "A".

For all electrodes of the cochlear implant implanted in cochlea "A", the "base-line" signal is compared with the "attenuated" signal. The one or more electrode contacts of the cochlear implant in cochlea "A" showing the biggest impact (e.g., as shown and described in more detail below in FIGS. 9A-10B) due to the contralateral masker is defined as "frequency-matched" to the applied masking signal (noise restricted to a particular frequency or a particular stimulation electrode contact) in cochlea "B".

Figure 9B:
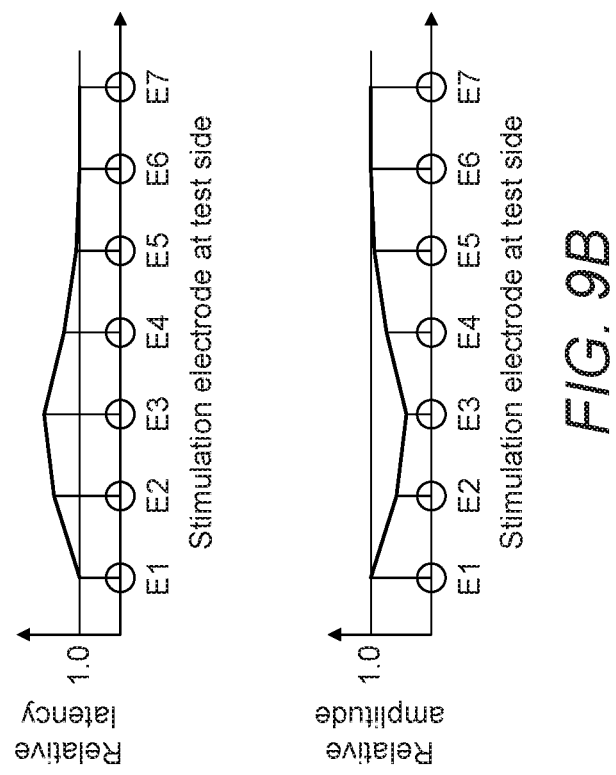
FIG. 9B shows the change in amplitudes and latencies of CAP recordings for the attenuated measurement compared to the baseline measurement of FIG. 9A according to embodiments of the present invention.
Figure 9A:
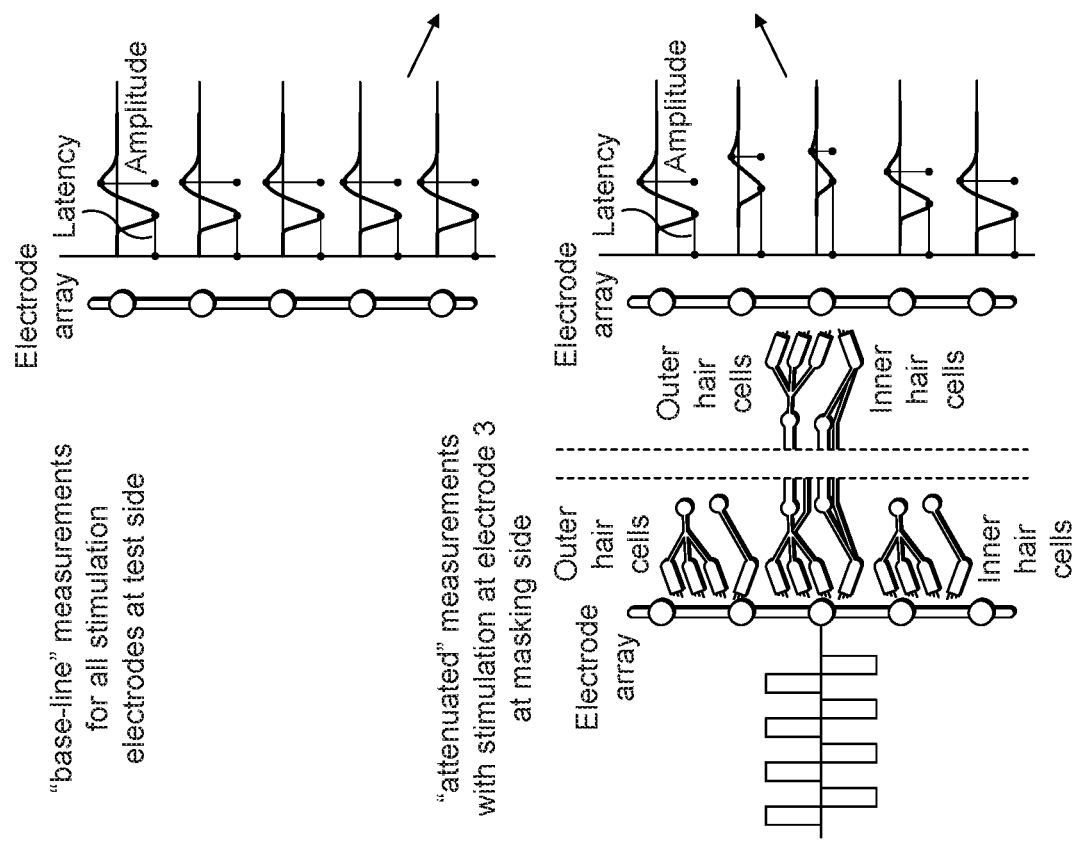
FIG. 9A shows a schematic view of exemplary baseline and attenuated measurements.

As shown in FIG. 9A when cochlea "B" also includes a cochlea implant, the predefined measurement setup includes a single stimulation pulse (applied at a single electrode contact and recorded at another electrode contact at the test side) for each electrode contact on the array. Therefore, the "base-line" signals at the test side ("A") are single eCAP recordings. The "attenuated" signals are derived using a pulse train at a certain electrode contact of the masking side ("B") as masker noise and a simultaneous, single stimulation pulse at the test side (as used for the "base-line" signals) are applied. Again, as for "base-line" signals, "attenuated" signals are represented by single eCAP recordings. For the derived single eCAP recordings, the latency of the minimum and the amplitude between the minimum and the maximum are regarded as characteristic parameters. For both parameters (latency and amplitude), the relative magnitude of the "attenuated" signal compared to the "base-line" signal is shown in FIG. 9B, where the change in latency as well as in amplitude (determined based on the minima and maxima of the eCAP) of the recorded ECAP is shown. For single eCAP recordings, all parameters concerning the morphology and intensity are suitable. Instead of single eCAP recordings, sequences of recordings (e.g., Amplitude Growth Functions (AGF), Recovery Functions (RF), or Spread of Excitation Functions (SoE)) may be used, e.g., parameters where the amplitudes and latencies might be deduced (e.g., slope with threshold of an AGF, time of 50% recovery within an RF, range of spread within an SoE, etc.). The derived relative parameters may be plotted for each masking channel separately against the stimulation channel at the test side. The derived functions may be interpolated using exponential functions in order to determine a continuous pattern of attenuated, relative parameters.

The frequency matched stimulation side of a channel at the masking side might be between two electrode contacts at the test-side. In this case, the position with the most impact may be interpolated by any known interpolation method, and the model may be, for example, one of electrical field distribution within the cochlear. This case is not shown and only the magnitude of attenuation at particular stimulation electrode contacts of the test side are regarded for the parameter matrices shown in FIGS. 10A and 10B.

For the single sites of stimulation of interest at the test side, the relative magnitudes concerning a single masker channel are summarized in a vector. Additionally, all vectors derived for the different channels at the masking side may be condensed to a matrix. FIG. 10A shows a matrix for relative latencies, and FIG. 10B shows a matrix for relative amplitudes that may be derived. In FIGS. 10A and 10B, the single lines are summarizing the effects of a masking signal of single electrode contacts at the masking side, and the columns are the relative magnitudes of parameters of single electrode contacts at the test side. If more complex masker stimuli and test stimuli are used, the lines and columns of the derived matrices might reflect certain frequencies, e.g., if the stimuli used at the masker and test side are eliciting certain frequencies only. For simplicity, in the present example, single electrode contacts represent single frequencies.

For a selected channel at the masking side, the frequency-matched channel (i.e., the channel showing the biggest impact of the masker) at the test side is identified by selecting the corresponding line (reflecting channel at masker side) of the amplitude and latency matrices and determining the column with the smallest to largest entry (reflecting the channel at test side). The selection of the corresponding line for masking channel 3 and the determined frequency matched channel 3 at the test side is highlighted with bold numbers in FIGS. 10A and 10B and shown graphically in FIG. 9B.

Alternatively, for a selected channel at the test side, the frequency matched channel at the masking side can be selected. For a single column (channel at test side) of the amplitude and latency matrices, the line with the smallest to largest entry is selected (channel at masking side). The selection of the corresponding column for test channel 3 and the determined frequency matched channel 3 at the masker side is highlighted with italic numbers in FIGS. 10A and 10B and shown graphically in FIG. 9B. The metric used for selecting the smallest to largest entry of each matrix can be extended to two dimensions in order to take both alternatives (selection via lines and columns) simultaneously into account. In practice, multidimensional matrices (e.g., including amplitudes and latencies, deduced parameters from AGFs, RFs, or SoEs, etc.) with suitable multidimensional metrics (e.g., different weights for amplitudes and latencies) may be used.

Rather than applying tones at certain frequencies on the contralateral side, as described above for frequency matching the cochlear implant in the ipsilateral ear with the contralateral ear, white noise or pulse bursts, may be applied on the contralateral side. In this case, the efferent fibers are masked with the contralateral stimulus within the whole VIII nerve, which reduces the proportion of efferent fibers within the measured eCAP signal on the ipsilateral, test side. Therefore, the measured response is representing the auditory percept at a higher order. According to the representation of the auditory percept via eCAP signal considering both afferent and efferent nerve fibers and the strength of the afferent and efferent contribution, estimations based on eCAP recordings of THR and MCL may be strengthened.

For masker stimuli, a broad-band white noise may be used in order to mask a maximum number of efferent fibers responding to contralateral stimuli. On the test side (supplied with a cochlear implant), for a certain stimulation electrode contact, a "base-line" signal as well as an "attenuated" signal is measured. If a single pulse (or short pulse sequence at a low rate without any activation of ipsilateral efferent processes) is used as test stimulus, the difference in eCAP amplitude of "base-line" and "attenuated" signal is expected to be at ~30%. Using sequences of separated single-pulse test stimuli, "base-line" with "attenuated" Amplitude Growth Functions (AGF) and Recovery Functions (RF) can be measured. "Attenuated" AGFs are expected to have a steeper slope with a non-linear behaviour in contrast to "base-line" AGFs. "Attenuated" RFs are expected to show different refractory times than "base-line" RFs. Differences in eCAP morphology (e.g., latency of signal) are expected to be more pronounced for RFs than for AGFs.

The correlation of the determined eCAP threshold of the "base-line" AGFs with the psychophysical measures (MCL, THR) is limited in clinical practice. Since for "attenuated" AGFs, the relative number of afferent fibers contributing to the eCAP signal is higher, the correlation of "attenuated" eCAP threshold (the ratio of "base-line" and "attenuated" eCAP threshold) and MCL is increased. If a selected electrode is already frequency matched to contralateral stimuli, such as described above, the broad-band noise at the masker side can be separated for the particular matched frequency. The resulting "base-line" and "attenuated" eCAPs for stimuli at the selected electrode contact should show only minor differences. Since the loudness percept is different, the range of stimulation intensities for the test stimuli is increased. Thus, if an eCAP signal is weak, this procedure may help to get a more clear recording.

The effect of masked efferent nerve fibers is usually measured indirectly by regarding the attenuation of DP-OAE amplitude (with CAP recordings) due to the presence of contralateral stimulation. In animal studies, it was outlined that the attenuation due to medial olivocochlear (MOC) efferent neurons was largest within 2-13 seconds after onset of contralateral broadband noise. In this time frame, the steady-state suppression is considered to be stable. It is expected that up to 100 ms after the stop of the contralateral noise the peripheral status is unchanged.

For DP-OAE measurements, the noise should be applied at the maximal level where still no middle ear muscle reflex is visible. If the subject is sedated, the stimuli can be louder since middle ear muscle movements are suppressed. If the contralateral noise is applied only for a short period (~400 ms before ipsilateral stimulus), the sound pressure of the noise affects the attenuation at a higher magnitude than for a longer duration of the applied noise and might be chosen at a lower level. During the 2-10 ms period after onset of contralateral noise, tone pulses on the ipsilateral side are applied. Attenuation effects are expected to be largest for moderate loud ipsilateral stimuli and present for all frequencies, but largest for the characteristic frequency.

The attenuation is usually quantified as the necessary increase of sound pressure of the ipsilateral stimuli in order to elicit the same CAP with contralateral masking stimuli as was measured without contralateral stimuli. An alternative measure is the attenuation for absolute CAP amplitudes, which shows a decrease of typically about 20-25% for short term contralateral noise (duration ~400 ms) and even higher using longer durations of contralateral noise (>2 s) depending on the sound pressure level of the ipsilateral stimuli (higher attenuation for low sound pressure).

Some embodiments of the system may be implemented as hardware, software (e.g., a computer program product), or a combination of both software and hardware. For example, embodiments may be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the system. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although the above discussion discloses various exemplary embodiments of the invention, it should be apparent that those skilled in the art can make various modifications that will achieve some of the advantages of the invention without departing from the true scope of the invention.

What is claimed is:

1. A method of fitting a cochlear implant in an ipsilateral ear of a subject, the cochlear implant having an electrode array with one or more electrode contacts, the method comprising:
    applying broad-band white noise stimulus to a contralateral ear in order to mask efferent nerve fibers in the ipsilateral ear;
    applying a single pulse stimulus or a sequence of separated single pulse stimuli to the ipsilateral ear and then measuring evoked compound action potential (CAP) signals in the ipsilateral ear for an electrode contact during a refractory period;
    determining a CAP threshold for the electrode contact based on the CAP signals measured; and
    adjusting processing parameters of the cochlear implant based on the CAP threshold.

2. The method of claim 1, wherein the broad-band white noise stimulus is applied by an acoustical stimulation.

3. The method of claim 1, wherein the broad-band white noise stimulus is applied by an electrical stimulation.

4. The method of claim 3, wherein the electrical stimulation is applied with a second cochlear implant in the contralateral ear.

5. The method of claim 1, wherein the broad-band white noise stimulus is applied by a mechanical stimulation.

6. The method of claim 1, wherein the sequence of separated single pulse stimuli increases in stimulation duration and/or increases in stimulation amplitude in order to measure Amplitude Growth Functions (AGF) and/or Recovery Functions (RF).

7. The method of claim 1, further comprising applying stimulation to the ipsilateral ear before applying the sequence of separated single pulse stimuli to the contralateral ear and then measuring the attenuated CAP signals in the ipsilateral ear for the electrode contact during the refractory period.

8. The method of claim 1, further comprising:
    repeating applying the single pulse stimulus or applying the sequence of separated single pulse stimuli to the ipsilateral ear for a second electrode contact;
    measuring the CAP signals for the second electrode contact and determining a CAP threshold based on the CAP signals measured for the second electrode contact; and
    adjusting processing parameters of the cochlear implant based on the CAP threshold for the second electrode contact.

9. A system for fitting a cochlear implant in an ipsilateral ear of a subject, the cochlear implant having an electrode array with one or more electrode contacts and configured to generate a single pulse stimulus or a sequence of separated single pulse stimuli to the ipsilateral ear, the system comprising:
    a tissue stimulation device configured to generate broad-band white noise stimulus to a contralateral ear in order to mask efferent nerve fibers in the subject;
    one or more response measurement contacts configured to measure evoked compound action potential (CAP) signals for an electrode contact in the ipsilateral ear during a refractory period;
    a comparing module in communication with the one or more response measurement contacts and configured to receive the CAP signals and configured to determine a CAP threshold based on the CAP signals in the ipsilateral ear during the refractory period; and
    a parameter adjusting module in communication with the comparing module and configured to interface with the cochlear implant and to adjust processing parameters of the cochlear implant based on the CAP threshold.

10. The system of claim 9, wherein the tissue stimulation device is an acoustical device configured to deliver an acoustical stimulus to an outer or middle ear.

11. The system of claim 9, wherein the tissue stimulation device is a stimulation electrode configured to deliver an electrical stimulus to neural tissue of an inner ear.

12. The system of claim 11, wherein the stimulation electrode comprises a second cochlear implant configured to deliver the electrical stimulus to the neural tissue of the inner ear.

13. The system of claim 9, wherein the tissue stimulation device is a mechanical device configured to deliver a mechanical stimulus to an outer ear or skull.

14. The system of claim 13, wherein the mechanical device is a bone conduction transducer.

15. The system of claim 9, wherein the cochlear implant includes the one or more response measurement contacts configured to measure the CAP signals.

16. The system of claim 9, further comprising a tissue stimulation module in communication with the tissue stimulation device, the tissue stimulation module configured to generate stimulation signals that are sent to the tissue stimulation device, wherein the tissue stimulation device generates the broad-band white noise stimulus and the sequence of separated single pulse stimuli based on the stimulation signals.

17. The system of claim 16, wherein the tissue stimulation module is configured to generate the sequence of separated single pulse stimuli with increasing stimulation duration and/or stimulation amplitude.

* * * * *

UNITED STATES PATENT AND TRADEMARK OFFICE
CERTIFICATE OF CORRECTION

PATENT NO. : 10,576,281 B2  
APPLICATION NO. : 15/791728  
DATED : March 3, 2020  
INVENTOR(S) : Schwarz et al.

Page 1 of 1

It is certified that error appears in the above-identified patent and that said Letters Patent is hereby corrected as shown below:

In Column 13, Line 49, Claim 7, delete "attenuated"

Signed and Sealed this  
Ninth Day of June, 2020

Andrei Iancu  
*Director of the United States Patent and Trademark Office*